United States Patent [19]

Cosman

[11] 4,281,667
[45] Aug. 4, 1981

[54] SINGLE DIAPHRAGM TELEMETRIC DIFFERENTIAL PRESSURE SENSING SYSTEM

[76] Inventor: Eric R. Cosman, 872 Concord Ave., Belmont, Mass.

[21] Appl. No.: 895,954

[22] Filed: Apr. 13, 1978

Related U.S. Application Data

[62] Division of Ser. No. 697,948, Jun. 21, 1976, abandoned.

[51] Int. Cl.³ .............................................. A61B 5/00
[52] U.S. Cl. ...................................... 128/748; 73/722; 128/660
[58] Field of Search ............... 128/673, 675, 748, 660; 73/701, 708, 716–719, 722

[56] References Cited

U.S. PATENT DOCUMENTS

| | | | |
|---|---|---|---|
| 3,034,356 | 5/1962 | Bieganski et al. | 128/748 |
| 3,038,465 | 6/1962 | Allard et al. | 128/675 |
| 3,625,199 | 12/1971 | Summers | 128/748 |
| 3,720,108 | 3/1973 | Freitag | 73/722 |
| 3,722,373 | 3/1973 | Beach et al. | 73/716 X |
| 3,724,275 | 4/1973 | Battaglini et al. | 73/716 |
| 3,727,463 | 4/1973 | Intraub | 73/398 R |
| 3,757,770 | 9/1973 | Brayshaw et al. | 128/748 X |
| 3,853,117 | 12/1974 | Murr | 128/748 X |
| 3,859,484 | 1/1975 | Nelson | 73/716 X |
| 3,943,915 | 3/1976 | Severson | 73/406 X |
| 3,958,558 | 5/1976 | Dunphy et al. | 128/748 X |
| 4,014,319 | 3/1977 | Faure | 128/748 |
| 4,022,190 | 5/1977 | Meyer | 128/748 |
| 4,026,276 | 5/1977 | Chubbuck | 128/653 |
| 4,067,241 | 1/1978 | Corbett | 73/717 |
| 4,124,023 | 11/1978 | Fleischmann et al. | 128/748 |
| 4,127,110 | 11/1978 | Bullara | 128/748 |
| 4,141,348 | 2/1979 | Hittman | 128/748 |

OTHER PUBLICATIONS

Collins, C. C., *I.E.E.E. Trans. On Bio.-Med. Engng.*, vol. 14, No. 2, Apr. 1967, pp. 74–83.
Atkinson, J. R. et al., *Journ. of Neurosurgery*, 1967, vol. 27, No. 5, pp. 428–432.

*Primary Examiner*—Kyle L. Howell
*Attorney, Agent, or Firm*—Richard J. Birch

[57] ABSTRACT

A differential pressure sensing device is fully implanted in the body of a patient to monitor internal pressure such as intracranial pressure. A movable element in the sensor communicates with the internal pressure of the body to be measured on one side and the atmospheric pressure on the other, the latter communicated through the intact skin and a nearly coplanar membrane. The movable element's differential pressure dependent displacement changes a physical characteristic of the sensor, such as the resonant frequency of a tune L-C circuit, and the change is detected external to the body by a radiating detector system, such as a frequency swept radio frequency oscillator, by which the internal pressure is read out.

44 Claims, 14 Drawing Figures

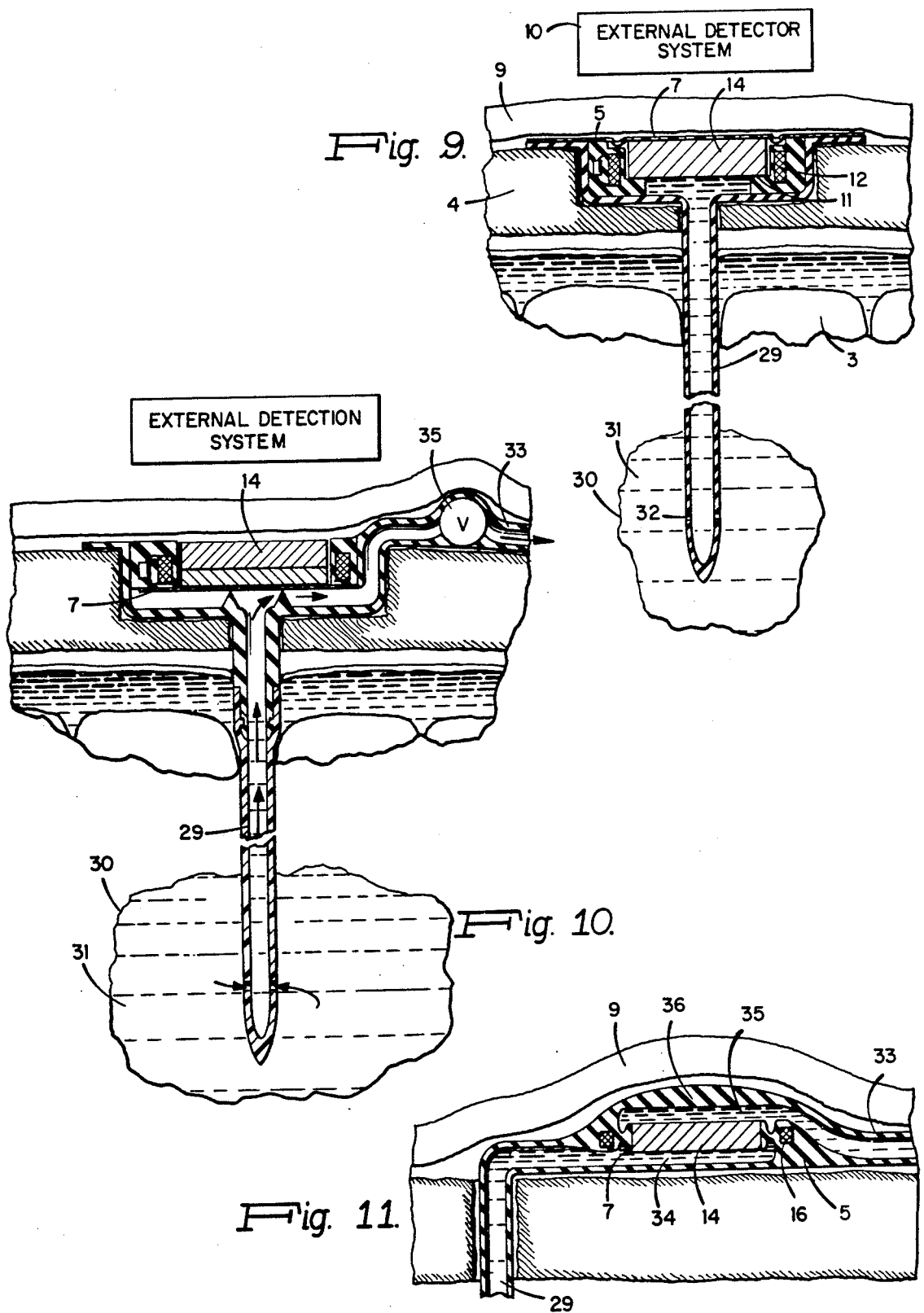

SINGLE DIAPHRAGM TELEMETRIC DIFFERENTIAL PRESSURE SENSING SYSTEM

CROSS REFERENCE TO RELATED APPLICATIONS

This application is a divisional application of Ser. No. 697,948, filed June 21, 1976 by Eric R. Cosman for A Telemetric Differential Pressure Sensing System and Method Therefore, now abandoned.

BACKGROUND OF THE INVENTION

The invention relates to the precision measuring and monitoring of pressures in the living body, such as intracranial pressure in the head, by means of a long-term, totally implanted sensor which undergoes a conformational change with pressure and which is coupled through the skin by electromagnetic, acoustic, or mechanical transmission to an external device which detects that change and interprets the pressure. The invention refers additionally to a device which is automatically barometric compensated, has immediate zero point reference check, can be made passive, and is insensitive to barometric or temperature changes.

At the present time there is no such wireless device available for general clinical or research purposes. The uses for such a device in neurosurgery would be immediate in the management of intracranial hypertension, monitoring of intracranial pressure in all cases of intracranial neurosurgery and head trauma, long-term diagnostics for evidence of tumor recurrence, and management of hydrocephalus.

All devices previously proposed have significant short-comings which make them impractical for widespread, safe, accurate, reliable, and long-term use as intracranial pressure monitors. Most designs involve a tube or wire connection through the skin to an external device, and since this greatly increases the chance of infection and electrical shock to the patient and reduces the patient's mobility they are hazardous and impractical. Of the devices which are wireless and fully implanted, they usually involve a sealed inner volume containing a fixed amount of gas, this being housed in a flexible container which deflects under pressure. The major problems with this design aspect are the following: liquids and gases will inevitably diffuse through the membranes and walls of the container causing steady drift of the zero-point reading, and causing an unpredictable error in the device's calibration; changes in barometric pressure will cause significant variations in the body pressure relative to the fixed volume pressure and thus the device's pressure readout must be corrected for barometric pressure changes in the external detection system; a trapped volume of significant size could make it dangerous for a patient to experience atmospheric pressure change, such as those found in air travel, for fear of rupturing the device; and temperature changes in the patient will cause changes in the trapped volume and resultant errors in the pressure reading. Previous totally implanted designs provide no means to check out their zero-pressure calibration after implantation and thus no means to determine diffusion or temperature drifts in the readings nor any check of the proper function of the device, which is essential for long and short-term implantation. Most previous designs are of complex construction, involve high tolerance parts and assembly, and are not amenable to calibration standardization; all of which make them expensive, inaccurate, and unsuitable for simple and general application.

Accordingly, some of the principal objects of the present invention are the following:

(1) To provide a pressure detector which can be implanted for an indefinite period under a fully intact skin with no wire or tube connections to the exterior so as to reduce infection and electrical shock hazard, and to read pressures in inaccessible spaces on the body, such as intracranial pressure, with an accuracy of 5 to 10% or better.

(2) To eliminate or make insignificant all inaccuracies, and dependencies on a trapped volume of gas or fluid in the device, to make the pressure readings insensitive to drifts from membrane permeability, barometric change, and temperature variation, and to eliminate the hazard of rupturing the device during air travel.

(3) To provide automatic barometric compensation as a built-in feature of the implanted device.

(4) To provide a means of easily and instantly checking the zero-pressure calibration of the device.

(5) To provide a sufficiently fast dynamic response to enable observation of variations in the body pressure due to heart rate, respiration, and any other physiological changes.

(5) To allow a simple calibration standardization of the implant.

(7) To allow the implanted device to be of simple, passive, compact, and low cost construction so as to be implanted permanently and to function properly for indefinitely long periods.

(8) To make the system amenable to telemetry over long distances so as to monitor pressures in a freely moving patient.

SUMMARY OF THE INVENTION

The above objects and advantages are achieved by the present invention as described in the following brief summary: The implanted pressure sensor comprises an insulating body with a movable element that moves through an opening or channel in the body. The movable element communicates with external atmospheric pressure on one side by means of a membrane which is nearly coplanar with the intact skin covering it, and with the internal pressure on the other side, by the same membrane, so that the degree of the movable element's displacement relative to the body is directly related to the difference in the internal and atmospheric pressures. Thus, since the pressure-dependent distortion of the implanted sensor does not involve variation of the volume of a trapped gas or space all problems related to the latter are eliminated. Also, since direct sensing of atmospheric pressure is exploited, barometric compensation is built-in and automatic. Further, the skin may be pressed manually just above the implanted device, and the movable element can be thus pushed back to a stop point in the device's body corresponding to equilibrium; thereby allowing the zero-point pressure position to be checked instantly at any time. The implanted device is coupled to an external detection system by electromagnetic, acoustic, or other radiation or transmission means across the intact intervening skin. The external detector system can determine the position of the movable element's displacement and thus the difference between the internal and atmospheric pressures. A variety of means of interrogating the implant by the external device are possible, but a particularly simple method involving a passive implant consists of building a fixed and parallel coil and capacitor combination into the body of the implant and a magnetic material into the movable element which moves through the coil, thus varying its inductance with varying displacement or internal pressure. The internal L-C resonant circuit is coupled electromagnetically to an external swept oscillator pickup circuit which detects the resonant frequency of the L-C circuit and related it to the coils plus magnetic material's inductance and corresponding internal pressure. As will be shown below, this construction is simple, compact, economical, free of thermal, diffusion, or mechanical drifts, calibration standardized, fast responding, adaptable to remote telemetry, and incorporable in a large number of multiple function implant configurations.

A fuller understanding of the invention and additional objects, advantages, and novel aspects of it will be gained from the following detailed description, illustrative drawings, and various embodiments and implementations. There are many design variations on the present invention concept which are possible, such as, constructional details, choice of specific conformations, various methods of coupling and information transfer from implant to external detector, and variations on the electronic design within the state of current electrical engineering art of both implanted and external circuitry. Such variations which are included within the scope of the claims below are understood to be included in the present invention disclosure. Furthermore, although the present inventive concept may be adapted to pressure measurement in numerous locations in the human body, it is highly illustrative to show its application as an intracranial pressure monitor. It is understood that the scope of the invention covers the use in areas of the body other than just the head.

DESCRIPTION OF THE DRAWINGS

In the following drawings similar reference characters represent similar parts.

FIG. 9 shows a view in vertical section of another more compact variation of the concepts of FIGS. 1 and 2 utilizing a single membrane and being incorporated in a system for measuring intraventicular pressure.

FIG. 10 shows a design similar to that in FIG. 9 but working in conjunction with a cerebrospinal fluid shunt valve.

FIG. 11 illustrates differential sensor of pressures in two different regions.

Referring to FIG. 1, the major elements of the implanted pressure sensor, used in this example as a monitor of epidermal intracranial pressure if the dural membrane 1 is intact or of cerebrospinal fluid 2 pressure that surrounds the brain 3 if the dura 1 is cut, may be understood as follows: The sensor, which is inserted in a burr hole drilled in the skull 4 comprises a housing 5 having a through opening in which travels a movable element 6. A flexible diaphragm 7 attached to housing 5 communicates on one side with the intracranial pressure P(ICP) and communicates on the other side with the pressure of the atmosphere 8, P(ATM), which is transmitted across the intact scalp 9. The diaphragm 7 is also attached to element 6. By this system, a difference in P(ICP)−P(ATM) will cause a force imbalance on the diaphragm 7, and by properly spring loading the movable element 6 relative to the housing 5 a calibrated relationship of the displacement of the movable element relative to the housing can be achieved.

This displacement will cause calibrated physical or electrical changes in some characteristic or parameter within the sensor, and these changes are detected by an external detection system 10 which is coupled to the sensor by electromagnetic, acoustic, or other means across the skin, but not through the skin as by a tube or wire. The detector 10 thus interpretes the displacement and reads out the associated barometrically compensated intracranial pressure P(ICP)−P(ATM). A mechanical stop, fiducial, or shoulder 11 is employed to interrupt the downward movement of the movable element relative to the housing so that by pressing on the skin just above diaphragm 7 an instant check of the zero-point of P(ICP)−P(ATM) can be made.

Figure 1:
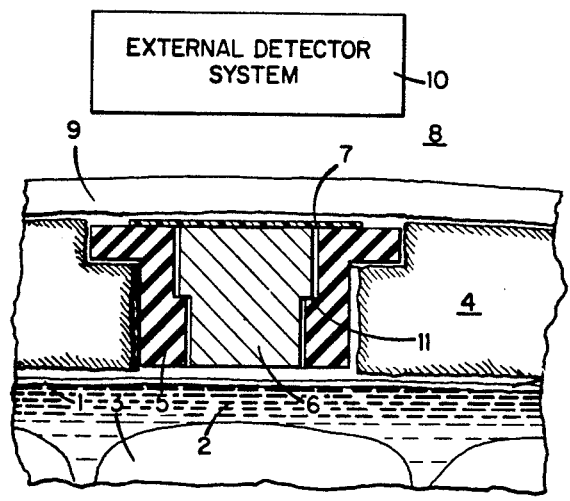
FIG. 1 shows a schematic, vertical sectional view of an implanted sensor being used to measure intracranial pressure in a living human being.
Figure 2:
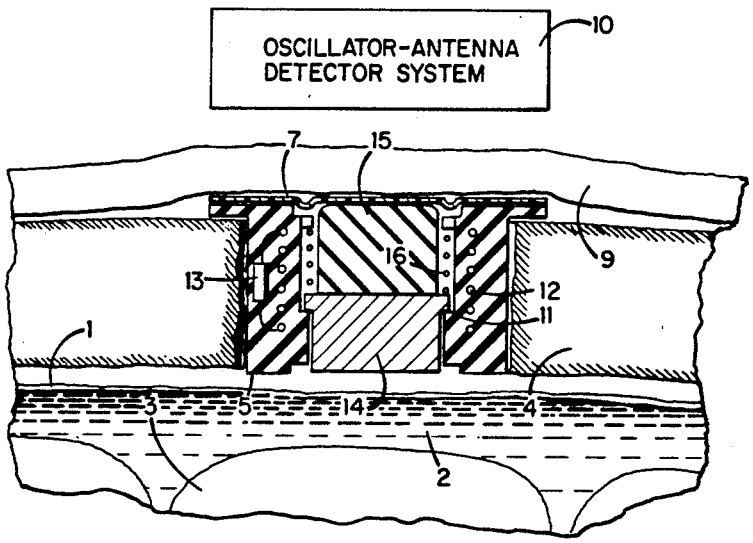
FIG. 2 shows a view in vertical section of a more specific design of the invention concept of FIG. 1 for intracranial pressure measurement.

Referring to FIG. 2, a specific and practical design involving the basic inventive concepts of FIG. 1 is shown. The cylindrical housing 5 is formed of an insulating plastic, such as, nylon or "Lexan", and has an upper flange so that it seats in a standard burr hole in the skull 4. A fixed coil 12 and capacitor 13 are embedded in the housing to form a parallel L-C tank circuit. A slug 14 of magnetic material moves in a cylindrical hole through the housing 5 and is attached to a coaxial cylindrical member 15, made of a plastic material, to form the movable element 6 of FIG. 1. The diaphragm 7 is made of thin plastic material, preferably convoluted for flexibility, and hermetically attached to housing 5. The diaphragm contacts the end of slug 14 or cylindrical member 15. The diaphragm 7, in combination with the slug 14 and member 15, have end-for-end symmetry such that P(ICP) is felt on one end, P(ATM) is communicated through the intact skin and is felt on the other end, and the external force on the slug 14 and member 15 is directly proportional to the difference $\Delta P = P(ICP) - P(ATM)$.

When P(ICP) is greater than P(ATM), the magnetic slug 14 will move upward relative to coil 12, thus changing the inductance of the coil-magnetic slug system. This, in turn, will cause a change in the resonant frequency of the L-C tank circuit, which is detected outside the body by an external detector system 10 described below. The magnetic slug 14 moves against a spring 16 so that the amount of its displacement x is proportional to the pressure imbalance $\Delta P$; i.e., $\Delta P = P(ICP) - P(ATM) = kx$, where k is the spring constant. Thus the change in resonant frequency of the L-C circuit can be directly related to $\Delta P$.

Figure 3:
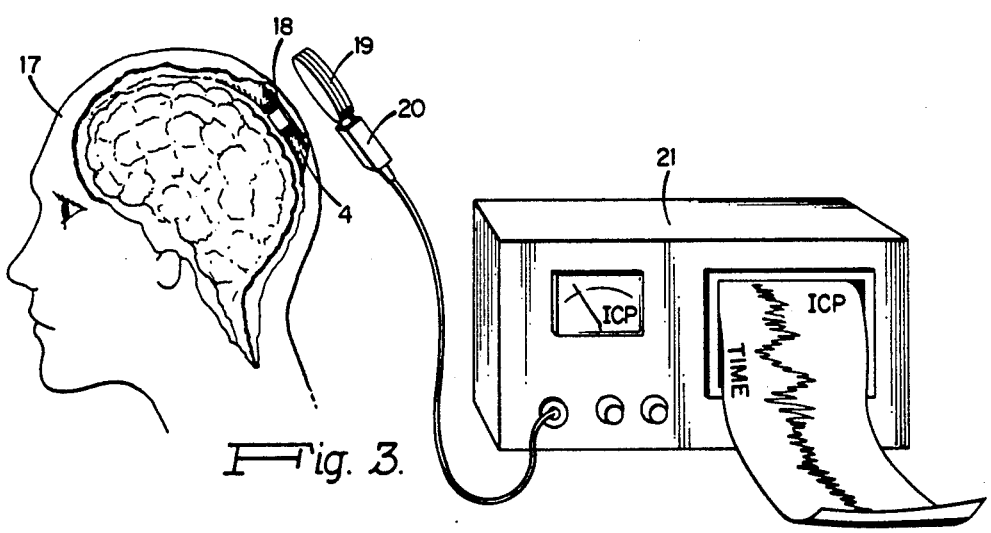
FIG. 3 illustrates the arrangement of the sensor such as that in FIG. 1 relative to the external "grid-dip" type oscillator with pickup antenna and the other associated circuitry for signal analysis and digital or chart recorder readout of the intracranial pressure.

Detection of the sensor's L-C resonant frequency, and thus the atmospherically compensated intracranial pressure can be easily accomplished by coupling the sensor's L-C circuit electromagnetically to the external antenna-oscillator system 10 which can detect a power dip at the resonant L-C frequency. Such detector circuits have been well known in radio engineering for decades as "grid-dip" oscillators and now can be made very compactly with integrated circuits. Such dip oscillators operate typically at 10 to 100 Mega Hertz and are swept over the resonant frequency at audio rates. The resonant power dip signal is detected by common peak detection methods. FIG. 3 illustrates a typical arrangement of patient 17, sensor 18, and external detection system. The external pickup antenna 19 can be coupled satisfactorily at several inches from the patient's head and forms the inductance of the swept oscillator contained in box 20. The frequency dip signal of the oscillator is analyzed in console 21 and displayed by analog or digital meters or by chart recorder.

The novel features of the external communication of the sensor through the skin and the provision of a shoulder stop 11 for elements 14 and 15 against the housing 5 at equilibrium position, not only allow an instant zero pressure reference check, but also insures an instant check of the operation of the entire system and correction of any temperature dependent variations in the electro-mechanical characteristics of the sensor. The coil 12 and capacitor 13 can easily be selected for negligible temperature drift and high resonant Q. The cylindrical elements 14 and 15 can be teflon coated and axially suspended on diaphragm 7, so that friction is minimized and the static and dynamic response and sensitivity are maximized.

The design has been demonstrated in implantations to detect differences in intracranial pressure of less than 5 mm of $H_2O$ and to record easily the rapid pressure variations due to heart beat and respiration, these being important clinical indications of a working system which previous designs cannot achieve. The diaphragm 7 and element 6 may be arranged coplanar with the scalp 9 and dura 1, respectively, during equilibrium so that surface tension effects of the scalp are minimized and fibrosis of the dura will not occur in long implantations, a problem which has plagued previous designs. The sensor is cosmetically inobtrusive, lying flat with the scull 4, and a full range of clinically important pressure from 0–100 cm of water may be read with only ½ mm total displacement of cylinder 14 and 15. The design of FIG. 2 can be made less than ½ inch in diameter and as shallow as 3 to 11 mm total height, making them adaptable to infants or small animals as well as adults. The design is easily calibration standardized by selection of construction materials and springs of accurate spring constant k. The design is intrinsically simple for high volume, low manufacture. It can be made of biocompatible material and covered with a thin silicone rubber enclosure.

It is understood that many variations of the basic concepts disclosed in FIGS. 1, 2 and 3 are possible and included in this disclosure. The element 6 may be a rigid mechanical means such as a cylinder or linkage. The physical characteristics of the sensor which is changed and detected with change of differential pressure $\Delta P = P(ICP) - P(ATM)$ may be diverse, and accordingly, so may be the detection means. For example, referring to FIG. 1, the body 5 and movable element 6 may be scatterers or absorbers of mechanical, acoustic, or ultrasonic waves or of electromagnetic waves such as micro waves or infrared radiation and the external detection system 10 may involve a source, interferometer, echo detector, frequency of amplitude detector of these waves by which the configuration or displacement of 6 relative to 5 may be determined. Unlike the design of FIG. 2, the sensor may contain active circuits with stored energy cells or induction power circuits. Many variations of the passive L-C circuit system of FIG. 2 and 3 are possible, involving other kinds of variable inductors, variable capacitors, both variable inductors and capacitors, or variable resistors to change the resonant frequency or impedance with pressure. Wide latitude is possible in choice of geometry, size, configuration of components, coil and ferrite geometries, and frequency of the design of FIG. 2. The magnetic slug may be replaced by a conductive metal slug to achieve induction change by eddy current detuning. The coil spring 16 may be replaced by a leaf, lever, or strap springs affixed to the body 5 at one end and to the movable cylinder 14 plus 15 in FIG. 2 or 6 in FIG. 1. The diaphragm may be convoluted as a speaker or rolling diaphragm or as a usual cylindrical bellows to achieve flexibility. The diaphragm may be metal or metal-coated or made of a variety of strong, impermeable, and flexible materials.

Figure 4:
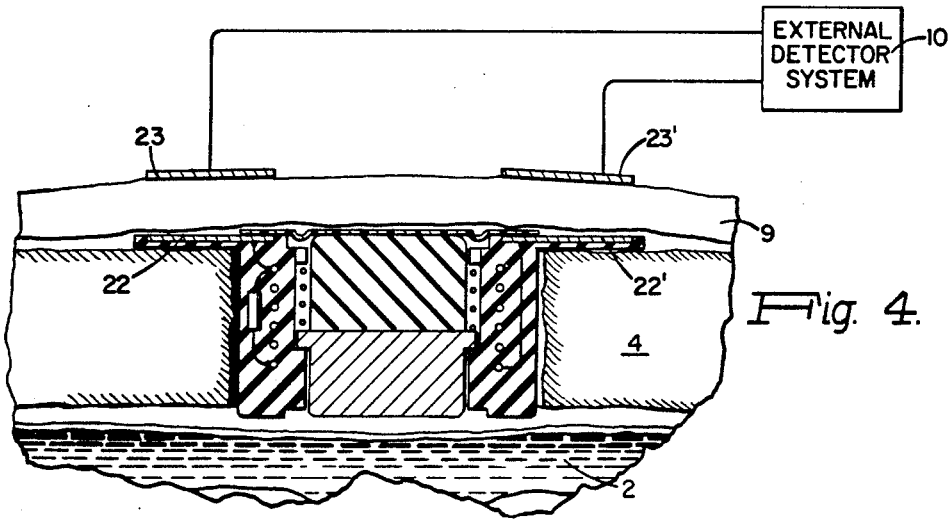
FIG. 4 shows another variant of the design of FIG. 2 in which a capacitive type electronic coupling through the skin is used to determine the resonant frequency of the internal L-C circuit.
Figure 5:
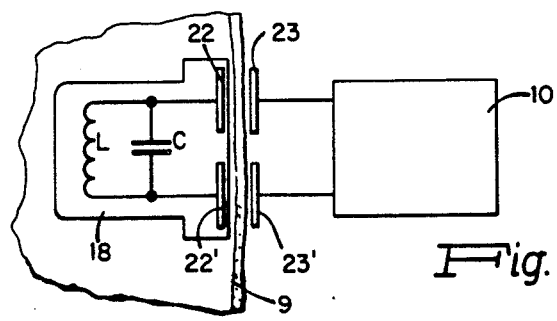
FIG. 5 is a schematic circuit and block diagram illustrating the method used in FIG. 4.

Other specific embodiments of the invention concept of FIG. 1 are possible in which substantively different external coupling means from that of FIG. 2 are used. FIGS. 4 and 5 illustrate an example of a sensor which incorporates an L-C resonant circuit similar to that in FIG. 2 but different method of electromagnetic coupling across the skin 9 to the external detector system 10. The coupling method is transcutaneous capacitive coupling and is done by area electrodes 22 and 22' near the upper surface of the sensor. These are in proximity to electrodes 23 and 23', respectively, on the skin. At the L-C resonant frequency the capacitive reactance of these pairs of adjacent electrodes is small, and thus one can use the resonant frequency of the implanted L-C circuit to determine the frequency of oscillation of an external strongly coupled oscillator housed in 10 which can then be measured by the analyzer-readout console. This type of sensor coupling has several important advantages. First it allows a nearby stable and fixed coupling, and circumvents the possible problems of holding pickup coil 19 of FIG. 3 near the sensor 18. In addition, it would allow for a compact transmittor system in 10 so that the intracranial pressure information may be telemetered to a remote monitoring console, while the compact battery operated oscillator is carried along with the patient or animal under examination. Thus the design of FIGS. 4 and 5 represents a unique system with all the advantages of the concepts of FIGS. 1, 2 and 3 as well as the capability of performing intracranial pressure studies and monitoring a great variety of subject activities.

It is understood that variants of the transcutaneous coupling scheme of FIGS. 4 and 5 are assumed in this disclosure. For example, whereas in FIGS. 4 and 5 an inductor L and capacitor C are built into the sensor, either one of which or both of which may vary with pressure, it is also possible that only the pressure sensing inductor L, or capacitor C, may be in the implanted sensor, and that the other element of the L-C circuit, C or L respectively, may be in the external system 10 along with the strongly coupled oscillator.

Figure 6:
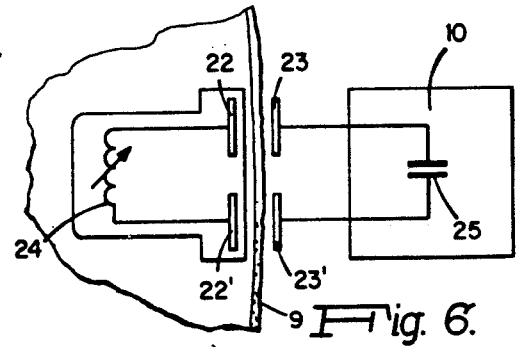
FIG. 6 illustrates schematically another means of coupling through the skin.

Referring to FIG. 6 the variable pressure sensing inductor 24 is coupled transcutaneously by area electrode pairs 22 and 22' and 23 and 23' to an external capacitor 25 which is integrated into the active external oscillator system that is contained in the external detection system 10. The frequency of oscillations of the external oscillator in 10 is determined by the L-C circuit made up of 24 and 25 and thus determines the balance condition and intracranial pressure which is read out by 10.

Figure 7:
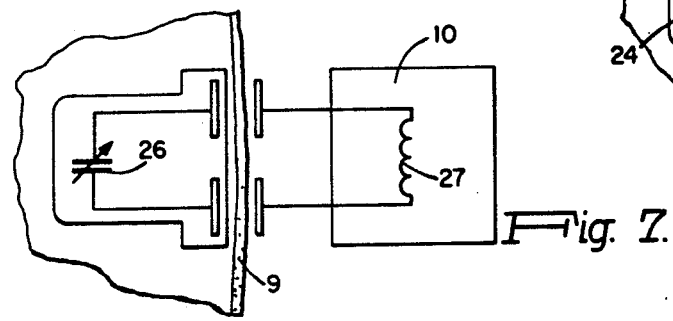
FIG. 7 illustrates yet another means of coupling through the skin.

Referring to FIG. 7, the implanted sensor contains the pressure sensitive capacitor 26, and the external active oscillator in 10 contains the complementary inductor 27.

Figure 8:
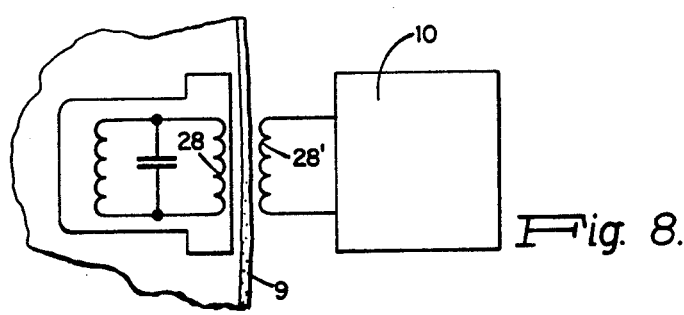
FIG. 8 is yet another coupling scheme.

Referring to FIG. 8, the transcutaneous coupling is shown to be inductive rather than capacitive. The implanted L or C may be pressure sensitive, or the implant may contain only L or only C analogously to FIG. 6 and FIG. 7. The implanted coil 28 is coupled to external coil 28', thus achieving the necessary coupling through the skin to the external oscillator in 10. Again, as in designs of FIGS. 5, 6 and 7 the frequency of the external oscillator is determined by the L-C value of the pressure sensitive tank circuit.

Other embodiments of the basic designs disclosed above can be devised for other types of pressure measurements within the body and head. To take as illustrative examples in the case of measuring intracranial pressure, the present invention can be used in conjunction with other functional devices, such as catheters, valves, shunts, flushing devices, reservoirs, filters, anti-siphon devices, and so on, to form a more diverse or multi-purpose intracranial pressure monitoring and control system. Some important illustrations are given below.

Referring to FIG. 9, the invention is shown connected to a ventricular catheter 29, which penetrates the brain 3 to the depth of the ventrical space 30 and samples the cerebrospinal fluid 31 therein through the holes 32. This device would then measure intraventricular fluid pressure. The catheter is usually made of silicone rubber and is an integral continuation of the encapsulation of the pressure sensor. Some variations in the designs of FIGS. 1 and 2 are also included in FIG. 9. The diaphragm 7 is attached to a ferrite or magnetic cylinder 14 with a thinner geometry of the coil 12 and sensor body 5. The magnetic cylinder may be spring loaded with its equilibrium position on the shoulder 11. In operation the hydrostatic pressure of the ventricular cerebrospinal fluid is transmitted to the inner side of the diaphragm 7 and the opposing atmospheric pressure is transmitted through the skin to the outer side of the diaphragm, and the magnetic slug's displacement is proportional to the difference in pressures. The barometric compensation, zero checking, and other features of the sensor of FIGS. 1 and 2 are the same. Such catheterization makes measurement of pressures in other parts of the body readily possible.

Referring to FIG. 10, the pressure sensor invention is attached to a ventricular cathetor 29 and the sampled ventricular fluid 31 is shunted past the sensor to the heart or stomach by a distal cathetor 33. A valve 34 is actuated by the diaphragm 7 so that as ventricular pressure rises the magnetic slug 14 and motion coupled diaphragm 7 move upward and the valve 34 increases its opening allowing more fluid to be shunted from the brain. Also shown is element 35, in series with the pressure monitor-shunt, which may be an on-off switch, reservoir, or one way flow control as usually built into systems for controlling hydroce phalus.

Referring to FIG. 11, the diagram illustrates the application of the invention as a differential pressure sensor of relative internal pressures within the body. Cathetor 29 communicates pressure of fluid pressure in the brain to the chamber 34 to the lower side of flexible diaphragm 7 which is attached to, and actually envelopes in FIG. 11, the magnetic material slug 14. The coil 12 is embedded in the body and the spring may be a flat spring also embedded in the body, or the sensor may rely on the elasticity of the flexible diaphragm 7 itself to provide the spring constant. Another cathetor 33 is attached to the body 5 and communicates pressure from a second anatomical region, such as the heart or peritoneum, to the upper chamber 35 and the upper side of flexible diaphragm 7. In operation a difference in pressures in chambers 34 and 35 would result in a force imbalance on 7 and 14 and the consequent displacement would be detected by an external detector system. Manual pressure on the skin 9 above the implanted sensor can deflect the outside wall 36 of chamber 35 causing it to indent so as to bring magnetic slug 14 against a seat or stop (not shown). Thus, the zero-point of the differential pressure sensor can be calibrated at any time after implantation.

Figure 12:
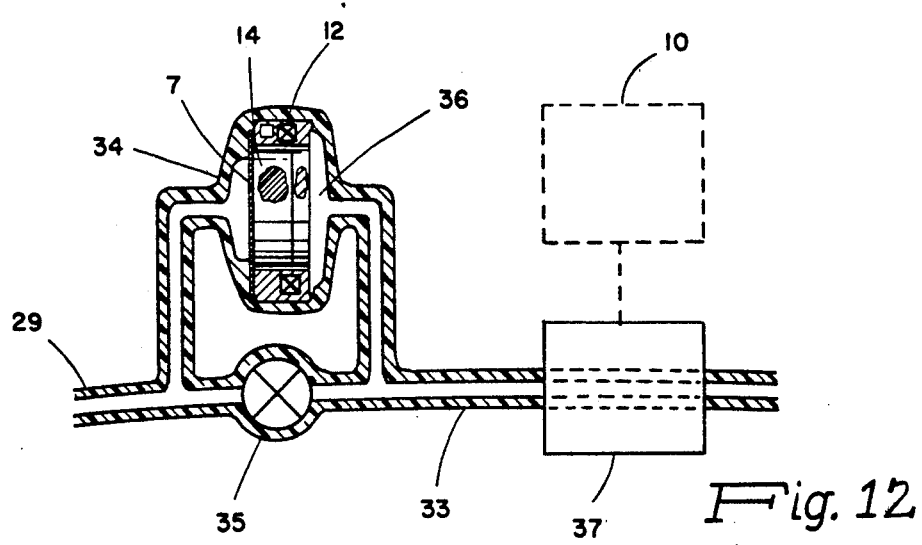
FIG. 12 illustrates a differential pressure sensor in combination with a fluid shunt valve and a fluid regulator.

Referring to FIG. 12, there is shown another configuration of the invention, used as a differential pressure sensor and combined with a fluid shunt valve and a fluid regulator or zeroing device 37. As in FIG. 11, the cathetor 29 communicates brain fluid pressure to chamber 34 and flexible diaphragm 7 as well as to the fluid shunt valve 35; and cathetors 33 and 33' communicate fluid pressure from another region, such as the heart, to the flexible diaphragm 7 and chamber 36 and carry exiting fluid away from valve 35. The difference in pressures are measured by the displacement of 14 relative to coil 12 as described above. This integral system thus serves to measure and regulate flow. In addition, device 37 interposed in cathetors 33 and 33' serves to allow an external pressure to be applied on the fluid in 33 and 36 so as to zero, the diaphragm 7 and 14. Device 37 may be, for example, a double domed flexible rubber reservoir which enables by a digital pressure through the skin closure of passage between 33 and 33' and subsequently, be a second manual pressure, an increase in the pressure in 36. Device 37 could also be a feedback controlled valve or switch, which, upon sensing the differential pressure across 34 and 36 by the external detector 10, a controlled feedback is used to actuate a valve in 37 in such a way as to drive the differential pressure in a desired direction. This feedback process could be carried out automatically by an electro-mechanical servo system or by manual manipulation on the skin.

Figure 13:
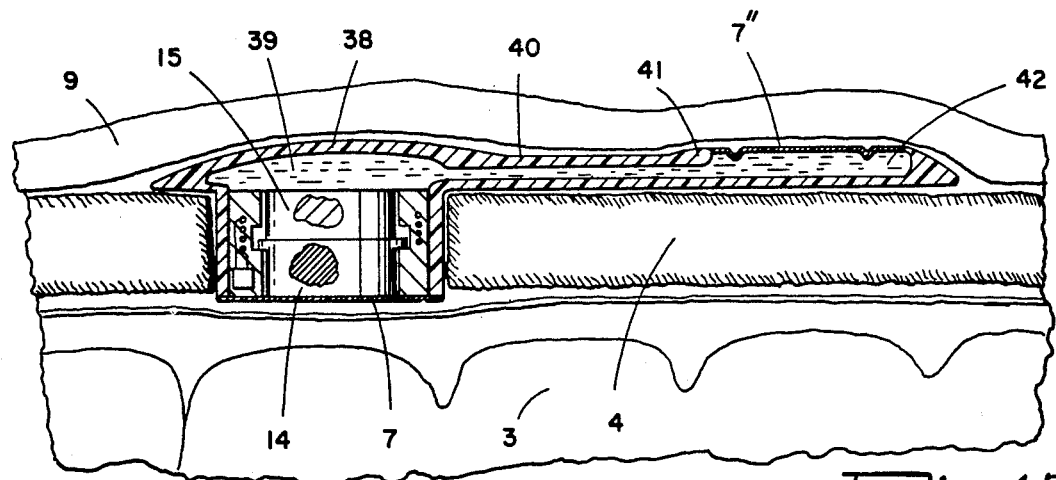
FIG. 13 illustrates a pressure sensor in which pressure is communicated to a diaphragm through a closed fluid system.

Referring to FIG. 13, another embodiment of the invention is illustrated for which the pressure communicated to the upper flexible diaphragm is supplied by a closed fluid system, rather than directly across the adjacent skin as in FIG. 2. In FIG. 13, a semi-rigid housing 38 covers cylinder 15 with a space 39 between them. The housing 38 is connected by a tube 40 to a second housing 41 which lies flat against the skull and which is covered on its upper side by a second flexible diaphragm 7', this communicating with the skin above it and thereby with the atmospheric or any other externally applied pressure on the skin. A fluid fills the volume 39, the tube 40, and the space 42 inside 41. The system is then a dual motion-coupled diaphragm arrangement. The first diaphragm 7, plus the magnetic piston 14 and the coaxial piston 15, act the same as described above, and the differential pressure on 7 is sensed by an external detector system. The pressure applied against 7 is now transmitted to it by the fluid-filled system comprising 38, 40, 41, and 7'. Barometric compensation again is automatic since atmospheric pressure on the skin above the second diaphragm 7' will be transmitted through the fluid to 7. An applied external pressure on the skin above 7' will also be transmitted to 7; and this could serve (a) to zero the magnetic piston 14 plus 15 and thus check the zero-point of the entire system, or (b) to supply a known and calibrated external pressure to 7 so as to balance the internal pressure on 7 and thus measure it by a pressure nulling method.

A configuration similar to that in FIG. 13 is possible where the differential pressure implant is cathetorized to measure a remote pressure in the ventricles, as was illustrated in FIGS. 9 and 10.

Figure 14:
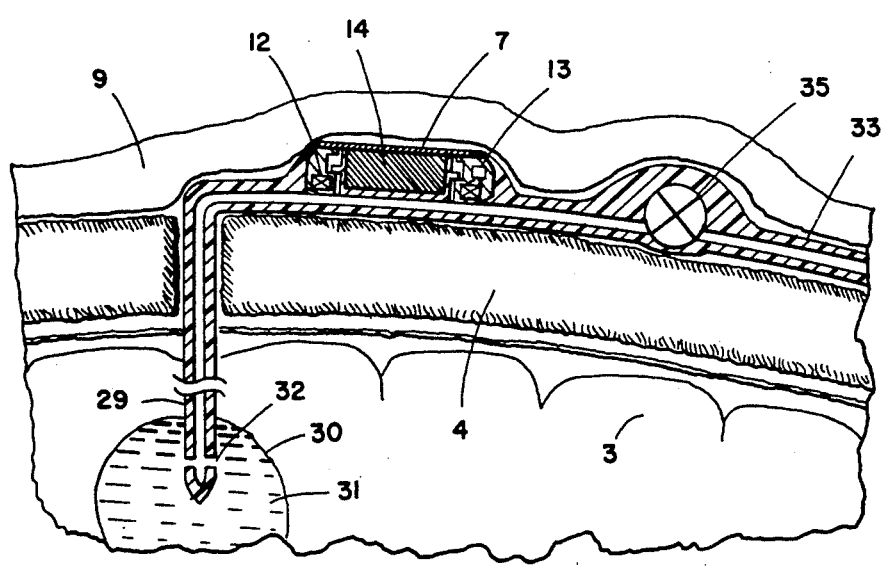
FIG. 14 illustrates another configuration similar to that shown in FIG. 10, except that the differential pressure sensor functions only as a pressure measuring device and not as a variable valve.

FIG. 14 illustrates a unified serial combination of the invention with a fluid shunt valve. This is similar to that in FIG. 10 except the differential pressure sensor acts only as a pressure measuring device and not as a variable valve too. The configuration is more compact and requires a smaller hole in the skull.

Having described in detail various embodiments of my invention, it will now be apparent to those skilled in the art that numerous modifications can be made therein without departing from the scope of the invention as defined in the following claims. For example, external manipulation of the diaphragm can be achieved by fluidly coupling a pressure source to the diaphragm by means of a fluid filled tube extending through the skin to the diaphragm.

What I claim and desire to secure by Letters Patent of the United States is:

1. An in vivo differential pressure sensor adapted for implantation in the living body and for in vivo calibration after implantation, said sensor comprising:
   (a) a housing having a means defining an opening therein
   (b) a single flexible diaphragm means which extends across the housing opening and is secured with respect to said housing, said single flexible diaphragm means having a first and a second side;
   (c) means allowing the first side of the single flexible diaphragm means to be in contact with and in mechanical pressure communication with a first bodily medium and allowing the second side of said single flexible diaphragm means to be in contact with and in mechanical pressure communication with a second bodily medium whereby a change in the difference of said pressures in the two bodily media will cause motion of at least a portion of said single flexible diaphragm means with respect to said housing;
   (d) means connected to said housing for contacting the single flexible diaphragm means for a predetermined relationship between the pressures on said two sides of said single flexible diaphragm means thereby defining a mechanical contact reference position of said single flexible diaphragm means with respect to said housing for a predetermined relationship between said pressures on said single flexible diaphragm means;
   (e) means having a preselected, detectable, variable parameter, the preselected, detectable variable parameter being detectable by detection apparatus located outside the living body, said means having a preselected, detectable variable parameter being at least in part cooperatively connected to and movable with said single flexible diaphragm means so that said preselected, detectable variable parameter will change with movement of said single flexible diaphragm means, such that the value of said preselected, detectable parameter can be detected at said mechanical contact reference position, said single flexible diaphragm means and said means having a preselected, detectable variable parameter being so constructed and cooperatively connected that said parameter value changes as a known function of the displacement with respect to said mechanical contact reference position of said single flexible diaphragm means and said displacement is a known function of the difference in pressures on the opposite sides of said single flexible diaphragm means; whereby when said sensor is implanted in the living body, the single flexible diaphragm means assumes said mechanical contact reference position when the pressure in said second bodily medium exceeds the pressure in said first bodily medium by said predetermining relationship thereby enabling the value of said preselected, detectable, variable parameter to be determined in vivo at said mechanical contact reference position, and whereby the value of said preselected, detectable, variable parameter is a measure of the difference in pressures in said two bodily media.

2. The sensor of claim 1 wherein said means having a preselected, detectable variable parameter is so constructed that said variable parameter can be calibrated as a function of the difference of pressures on the opposite sides of said single flexible diaphragm means prior to implantation of said sensor in the living body.

3. An in vivo differential pressure sensor adapted for implantation beneath the skin in the living body and sensing the pressure of a bodily fluid and adapted for in vivo calibration after implantation, said sensor comprising:
   (a) a housing;
   (b) a single flexible diaphragm means which is fluid pressure sealed with respect to said housing and having a first and a second side, at least a portion of said first side comprising at least a portion of the exterior surface of said sensor and being positioned so that after implantation, said portion of said first side is in mechanical pressure communication with the skin and whereby pressures external to the body can be communicated mechanically through the skin to said single flexible diaphragm, said single flexible diaphragm means and said housing together defining a chamber such that the second side of said single flexible diaphragm means communicates mechanically with pressure inside said chamber so that changes in the difference in pressure on said two sides of said single flexible diaphragm means causes a motion of at least a portion of said single flexible diaphragm means;

(c) inlet means to said chamber allowing the entrance of a bodily fluid from an internal bodily region to the inside of said chamber, thereby providing a fluid pressure communication between said internal bodily region and the inside of said chamber when said sensor is implanted in the living body, and enabling that a change in the difference of pressures in said internal bodily region will cause a movement of at least a portion of said single flexible diaphragm means with respect to said housing;

(d) contact means connected to said housing for contacting the single flexible diaphragm means for a predetermined relationship between the pressures on said single flexible diaphragm means thereby defining a mechanical contact reference position of said single flexible diaphragm means with respect to said housing at a predetermined relationship between said pressures on said single flexible diaphragm means;

(e) means having a preselected, detectable, variable parameter, the preselected, detectable variable parameter being detectable by detection apparatus located outside the living body, said means having a preselected, detectable variable parameter being at least in part cooperatively connected to and movable with said single flexible diaphragm means so that said preselected, detectable variable parameter will change with movement of said single flexible diaphragm means, said single flexible diaphragm means and said means having a preselected, detectable variable parameter being so constructed and cooperatively connected that said parameter changes as a known function of the displacement with respect to said mechanical contact reference position of said single flexible diaphragm means and said displacement is a known function of the difference in pressures on the opposite sides of said single flexible diaphragm; whereby when said sensor is implanted beneath the skin, said single flexible diaphragm means can be driven to said mechanical contact reference position by a pressure external to the living body applied to the skin adjacent to said sensor and said preselected parameter can be determined at said mechanical contact reference position after implantation corresponding to said predetermined pressure relationship, and whereby the value of said preselected, detectable, variable parameter is a measure of the pressure in said internal bodily region.

4. The sensor of claim 3 wherein said means having a preselected, detectable variable parameter is so constructed that value of the variable parameter can be determined at the mechanical contact reference position after implantation of said sensor, said parameter value corresponding to said predetermined pressure relationship.

5. The sensor to claim 3 wherein said means having a preselected, detectable variable parameter is so constructed that said variable parameter can be calibrated as a function of the difference of pressures on the opposite sides of said single flexible diaphragm means prior to implantation of said sensor in the living body.

6. The apparatus of claim 3 wherein said housing has an opening therein, said single flexible diaphragm means extending over said opening and being fluid pressure sealed with respect to said housing so that said sngle flexible diaphragm means and defines part of the exterior surface of said sensor and said single flexible diaphragm and means said housing defines said chamber.

7. The apparatus of claim 3 wherein said contact means defining a mechanical contact reference position includes electrode contacts that touch at a reference position of said single flexible diaphragm means relative to said housing, and said means having a detectable, variable parameter includes circuit means within said sensor and cooperative with said electrode contacts whereby the touching of said electrode contacts produces a characteristic response of said circuit that is detectable by apparatus outside said living body.

8. The apparatus of claim 3 wherein said contact means is connected to said housing so that the defined mechanical contact reference position corresponds to the balance of said pressures on opposite sides of said single flexible diaphragm means.

9. The apparatus of claim 3 wherein said inlet means comprises a tube.

10. The apparatus of claim 3 wherein the locus of points where said single flexible diaphragm means is sealed to said housing defines a perimeter which lies substantially in a plane, and wherein said single flexible diaphragm means is at least partially in coplanar geometry with respect to said plane for said predetermined pressure relationship.

11. The apparatus of claim 3 wherein said means having a preselected, detectable parameter comprises electronic circuit means, said parameter being a characteristic response parameter of said circuit means which is detectable by electromagnetic coupling to electronic apparatus means located external to said living body.

12. The apparatus of claim 11 wherein said electronic circuit means includes an inductor and further comprises a magnetic material which moves relative to the inductor with at least a portion of said single flexible diaphragm means, such movement producing a displacement of said magnetic material relative to said inductor thereby varying the inductance of said inductor.

13. The apparatus of claim 11 wherein said electronic circuit means includes an inductor and further comprises a conductive material which moves relative to the inductor with at least a portion of said single flexible diaphragm means, such movement producing a displacement of said conductive material relative to said inductor thereby varying the inductance of said inductor.

14. The apparatus of claim 11 wherein said electronic circuit means comprises a resonant electrical circuit which includes a coil and a capacitor.

15. The apparatus of claim 14 wherein said coil is fixed with respect to said housing.

16. The apparatus of claim 14 further comprising means for varying the capacitance of said capacitor in response to said displacement of at least a portion of said single flexible diaphragm means.

17. The apparatus of claim 14 wherein said resonant electrical circuit is a parallel resonant circuit and wherein said preselected detectable parameter is the resonant frequency of said resonant circuit.

18. The apparatus of claim 3 wherein said single flexible diaphragm means is spring loaded with respect to said housing.

19. The apparatus of claim 3 and further comprising an outlet means which permits the exit of fluid from the interior of said chamber.

20. The apparatus of claim 19 wherein said inlet and outlet means include tubes.

21. The apparatus of claim 19 further comprising a fluid shunt valve means interposed in series with at least one of said inlet or said outlet means for regulating the flow of said bodily fluid from said internal bodily region.

22. The apparatus of claim 19 comprising a fluid shunt valve means which is mounted in part on said single flexible diaphragm means and in part on said housing so that when at least a portion of said single flexible diaphragm means displaces under changes in said pressures on either side of said single flexible diaphragm means, there will result a change in the opening of said fluid shunt valve means so as to change the flow regulation of said bodily fluid.

23. The apparatus of claim 3 wherein said means having a preselected, detectable parameter includes at least a portion of said single flexible diaphragm means.

24. The sensor of claim 3 wherein said means having a preselected, detectable parameter comprises a scatterer of ultrasonic radiation.

25. An in vivo differential pressure sensor adapted for implantation beneath the skin in the living body and sensing the pressure of a bodily fluid and for in vivo zero point calibration after implantation, said sensor comprising:
  (a) a housing having means defining an opening therein;
  (b) a single flexible diaphragm means extending over the end of the housing opening and being fluid pressure sealed with respect to said housing, said flexible diaphragm forming part of the exterior surface of the sensor whereby when said sensor is implanted beneath the skin said single flexible diaphragm means is adjacent to and in pressure communication with the skin and whereby pressure external to the body applied to the skin is mechanically communicated to said single flexible diaphragm means, said single flexible diaphragms means and said housing forming a chamber with said single flexible diaphragm means communicating on one side with pressure inside the chamber and on the other side with pressure external to the sensor and adjacent to said single flexible diaphragm means;
  (c) inlet means to said chamber allowing the entrance of a bodily fluid from an internal bodily region to the inside of said chamber and thereby providing fluid pressure communication between said internal bodily region and said single flexible diaphragm so that a change in the difference of pressures on said single flexible diaphragm means will produce a movement of a portion of said single flexible diaphragm means with respect to said housing;
  (d) a magnetic material that is connected to and thus moves with said single flexible diaphragm means;
  (e) a parallel resonant circuit means comprising an inductor and a capacitor that are mounted within said housing so that the inductance of said inductor is varied in accordance with the position of the magnetic material relative to the inductor, the variation in said inductance producing a variation in the resonant frequency of the resonant circuit means, said inductor and magnetic material being so constructed and cooperatively related that the change in the resonant frequency is a known function of the change in the difference of said pressures on the opposite sides of said single flexible diaphragm means, said resonant frequency being detectable by apparatus external to the living body; and,
  (f) a mechanical stop for said single flexible diaphragm means against said housing when the pressure external to said sensor on said single flexible diaphragm means is equal to or greater than the pressure in said chamber; whereby when said sensor is implanted beneath the skin, said single flexible diaphragm means, can be driven to said mechanical stop by a pressure applied externally to the skin and said resonant frequency can be determined at said mechanical stop after implantation corresponding to the zero pressure difference across said single flexible diaphragm means, and whereby the value of said resonant frequency is a measure of the pressure in said bodily fluid.

26. The sensor of claim 25 wherein said parallel resonant circuit means is constructed so that the value of said resonant frequency can be determined at the mechanical stop of said single flexible diaphragm means after implantation of said sensor, said value of said resonant frequency at said mechanical stop corresponding to equal pressures on said single flexible diaphragm and thereby establishing an in vivo zero point calibration of said resonant frequency as a function of the difference in pressures on said single flexible diaphragm.

27. The sensor of claim 25 wherein said parallel reponant circuit means is constructed so that said resonant frequency can be calibrated as a function of the difference of pressures on the opposite sides of said single flexible diaphragm means prior to implantation of said sensor.

28. The sensor of claim 25 and further comprising an outlet means for allowing said bodily fluid to flow out of said chamber, the outlet means including a tubing.

29. The sensor of claim 28 and further comprising a fluid shunt valve means in series arrangement with at least one of said inlet or said outlet means so as to regulate the flow of said bodily fluid.

30. The sensor of claim 25 and further comprising a fluid reservoir in series with at least one of said inlet or said outlet means.

31. An in vivo differential pressure sensor adapted for implantation in the living body and sensing the pressure of a bodily fluid and for in vivo zero point calibration after implantation, said sensor comprising:
  (a) a housing having means defining an opening therein;
  (b) a single flexible diaphragm means extending over the end of the housing opening and being fluid pressure sealed with respect to said housing, said single flexible diaphragm means forming part of the exterior surface of the sensor, whereby when said sensor is implanted beneath the skin, said single flexible diaphragm means is adjacent to and in pressure communication with the skin and whereby pressure external to the body applied to the skin is mechanically communicated to said single flexible diaphragm means, said single flexible diaphragm means and said housing forming a chamber with said single flexible diaphragm means communicating on one side with pressure inside the chamber and on the other side with pressure external to the sensor and adjacent to said single flexible diaphragm means;

(c) inlet means to said chamber allowing the entrance of a bodily fluid from an internal bodily region to the inside of said chamber and thereby providing fluid pressure communication between said internal bodily region and said single flexible diaphragm means so that a change in the difference of pressures on said single flexible diaphragm means will produce a movement of a portion of said single flexible diaphragm means with respect to said housing;

(d) a conductive material that is connected to and thus moves with said single flexible diaphragm means;

(e) a parallel resonant circuit means comprising an inductor and a capacitor that are mounted within said housing so that the inductance of said inductor is varied in accordance with the position of the conductive material relative to the inductor, the variation in said inductance producing a variation in the resonant frequency of the resonant circuit means, said inductorand said conductive material being so constructed and cooperatively related that the change in the resonant frequency is a known function of the change in the difference of said pressures on the opposite sides of said single flexible diaphragm means, said resonant frequency being detectable by apparatus external to the living body; and, (f) a mechanical stop for said single flexible diaphragm means against said housing when the pressure external to said sensor on said single flexible diaphragm means is equal to or greater than the pressure in said chamber; whereby when said sensor is implanted beneath the skin said single flexible diaphragm means can be driven to said mechanical stop by a pressure applied externally to the skin and said resonant frequency can be determined at said mechanical stop after implantation corresponding to the zero pressure difference across said single flexible diaphragm means, and whereby the value of said resonant frequency is a measure of the pressure in said bodily fluid.

32. The sensor of claim 31 wherein said parallel resonant circuit means is constructed so that the value of said resonant frequency can be determined at the mechanical stop of said single flexible diaphragm means after implantation of said sensor, said value of said resonant frequency at said mechanical stop corresponding to equal pressures on said single flexible diaphragm means and thereby establishing an in vivo zero point calibration of said resonant frequency as a function of the difference in pressures on said single flexible diaphragm means.

33. The sensor of claim 31 wherein said parallel resonant circuit means is constructed so that said resonant frequency is calibrated as a function of the difference of pressures on the opposite sides of said single flexible diaphragm means prior to the implantation of said sensor.

34. The sensor of claim 31 and further comprising an outlet means for allowing said bodily fluid to flow out of said chamber, the outlet means including a tubing.

35. The sensor of claim 31 and further comprising a fluid shunt valve means in series arrangement with at least one of said inlet or said outlet means so as to regulate the flow of said bodily fluid.

36. The sensor of claim 31 and further comprising a fluid reservoir in series with either said inlet or said outlet means.

37. An in vivo pressure detecting system comprising in combination:

(a) a differential pressure sensor adapted for implantation in a living body and for in vivo calibration after implantation, said sensor comprising:

(1) a housing;

(2) a single flexible diaphragm means which is secured with respect to said housing and having a first and a second side, at least a portion of said first side comprising at least a portion of the exterior surface of said sensor and being positioned so that after implantation, said exterior surface portion of said first side is in mechanical pressure communication with the skin and whereby pressures external to the body can be communicated mechanically across the skin to said single flexible diaphragm means;

(3) means allowing the second side of said single flexible diaphragm means to be in contact and pressure communication with a bodily medium the pressure of which is to be sensed when said sensor is implanted in the living body, so that a change in the difference in pressures on said two sides of said single flexible diaphragm means causes a motion of at least a portion of said single flexible, diaphragm means with respect to said housing;

(4) contact means connected to said housing for contacting the single flexible diaphragm means for a predetermined relationship between the pressures on said single flexible diaphragm means thereby defining a mechanical contact reference position of said single flexible diaphragm means with respect to said housing for a predetermined relationship between said pressures on said single flexible diaphragm means;

(5) means having a preselected, detectable, variable parameter that is detectable by detection apparatus located outside of the living body, said means having a preselected, detectable variable parameter being at least in part cooperatively connected to and movable with said single flexible diaphragm means so that said preselected, detectable variable parameter will change with movement of said single flexible diaphragm means, said single flexible diaphragm means and said means having a preselected, detectable variable parameter being so constructed and cooperatively connected that said preselected, detectable variable parameter changes as a known function of the displacement with respect to said mechanical contact reference position of said single flexible diaphragm means and said displacement is a known function of the difference in pressures on the opposite sides of said single flexible diaphragm means, whereby when said sensor is implanted beneath the skin, said single flexible diaphragm means can be driven to said mechanical contact reference position by a pressure external to the living body applied to the skin adjacent to said sensor and whereby the value of said preselected detectable, variable parameter can be determined at said mechanical contact reference position after implantation, said parameter value corresponding to said predetermined pressure relationship, and whereby the value of said preselected, detectable, variable parameter is a measure of the pressure in said bodily medium; and, (b) means for detecting said preselected, detectable, variable parameter value of said preselected, detectable variable parameter at said mechanical contact reference position and any variation therefrom when said sensor is implanted in a living body, said detecting means being located externally of the living body and without any connection to said sensor which requires a break in the skin of the living body.

38. The system of claim 37 wherein said means having a preselected, detectable variable parameter is so constructed that said variable parameter is calibrated as a function of the difference of pressures on the opposite sides of said single flexible diaphragm means prior to implantation of said sensor in a living body.

39. An in vivo pressure detecting system comprising in combination:
   (a) an in vivo differential pressure sensor adapted for implantation beneath the skin in the living body and sensing the pressure of a bodily fluid, and adapted for in vivo calibration after implantation, said sensor comprising:
     (1) a housing;
     (2) a single flexible diaphragm means which is fluid pressure sealed with respect to said housing and having a first and a second side with at least a portion of said first side comprising at least a portion of the exterior surface of said sensor and being positioned so that after implantation, said portion of said first side is in mechanical pressure communication with the skin and whereby pressures external to the body can be communicated mechanically across the skin to said single flexible diaphragm means said single flexible diaphragm means and said housing together defining a chamber such that the second side of said single flexible diaphragm means communicates mechanically with pressure inside said chamber so that changes in the difference in pressures on said two sides of said single flexible diaphragm means causes a motion of at least a portion of said single flexible diaphragm means;
     (3) inlet means to said chamber allowing the entrance of a bodily fluid from an internal bodily region to the inside of said chamber when said sensor is implanted in the living body, thereby providing a fluid pressure communication between said internal bodily region and the inside of said chamber when said sensor is implanted in the living body, and enabling that a change in the pressure in said internal bodily region will cause a movement of at least a portion of said single flexible diaphragm means with respect to said housing;
     (4) contact means connected to said housing for contacting the single flexible diaphragm means for a predetermined relationship between the pressures on said single flexible diaphragm means thereby for defining a mechanical contact reference position of said single flexible diaphragm means with respect to said housing at a predetermined relationship between said pressures on said single flexible diaphragm means;
     (5) means having a preselected, detectable, variable parameter that is detectable by detection means located outside the living body, said means having a preselected, detectable variable parameter being at least in part cooperatively connected to and movable with said single flexible diaphragm means so that said preselected, detectable variable parameter will change with movement of sa single flexible diaphragm means, said single flexible diaphragm means and said means having a preselected, detectable variable parameter being so constructed and cooperatively connected that said preselected, detectable variable parameter changes as a known function of the displacement with respect to said mechanical contact reference position of said single flexible diaphragm means and said displacement is a known function of the difference in said pressures on the opposite sides of said single flexible diaphragm means, whereby when said sensor is implanted beneath the skin, said single flexible diaphragm means can be driven to said mechanical contact reference position by a pressure external to the living body applied to the skin adjacent to said sensor and whereby the value of said preselected, detectable, variable parameter can be determined at said mechanical contact reference position after implantation, said parameter value corresponding to said predetermined pressure relationship, and whereby the value of said preselected, detectable, variable parameter is a measure of the pressure of said bodily fluid; and,
   (b) means for detecting said preselected, detectable, variable parameter value of said preselected, detectable variable parameter at said mechanical contact reference position and any variation therefrom when said sensor is implanted in a living body, said detecting means being located externally of the living body and without any connection to said sensor which requires a break in the skin of the living body.

40. The system of claim 39 wherein said means having a preselected, detectable variable parameter is so constructed that said variable parameter can be calibrated as a function of the difference of pressures on the opposite sides of said single flexible diaphragm means prior to implantation of said sensor in a living body.

41. An in vivo differential pressure sensor adapted for implantation in the living body and in vivo calibration after implantation, said sensor comprising:
   (a) a housing having means defining an opening extending therethrough;
   (b) a single flexible diaphragm extending across said housing opening and secured to said housing, said flexible diaphragm communicating mechanically with pressures in two separate bodily regions external to the sensor that are separated by the flexible diaphragm means with the pressure in one of the bodily regions being in internal bodily pressure to be measured when the sensor is implanted in a living body;
   (c) contact means connected to said housing for contacting the single flexible diaphragm means for a predetermined relationship between the pressures on said single flexible diaphragm means thereby defining a mechanical contact reference position of said single flexible diaphragm with respect to said housing for a predetermined pressure relationship in said bodily regions; and, (d) means having a preselected, detectable, variable parameter, the preselected, detectable variable parameter being detectable by detection means located outside the living body, said apparatus having a preselected, detectable variable parameter being at least in part cooperatively connected to and movable with said single flexible diaphragm means so that said preselected, detectable variable parameter will change with movement of said single flexible diaphragm means, said single flexible diaphragm means and said means having a preselected, detectable variable parameter being so constructed and cooperatively connected that said preselected, detectable variable parameter changes as a known function of the displacement with respect to said mechanical contact reference position of said single flexible diaphragm means and said displacement is a known function of the difference in said pressures on the opposite sides of said flexible diaphragm, and whereby the value of said preselected, detectable, variable parameter can be determined at said mechanical contact reference position after implantation by increasing the pressure in one of said internal bodily regions so as to drive said single flexible diaphragm to said mechanical contact reference position thereby calibrating the sensor in vivo, said parameter value corresponding to said predetermined pressure relationship, and whereby changes in said preselected, detectable variable parameter from said mechanical contact reference position are a measure of the pressure in said internal bodily region.

42. An in vivo differential pressure sensor adapted for implantation beneath the skin in the living body and for in vivo zero point calibration after implantation, said sensor comprising:

(a) a housing;

(b) a single flexible diaphragm means which is secured with respect to said housing; and having a first and a second side, at least a portion of said first side defining at least a portion of the exterior surface of said sensor and being positioned so that after implantation, said portion of said first side is in mechanical pressure communication with the skin and whereby pressures external to the body can be communicated mechanically across the skin to said single flexible diaphragm means;

(c) means allowing the second side of said single flexible diaphragm means to be in contact with and in mechanical pressure communication with aa bodily medium, the pressure of which is to be sensed when said sensor is implanted in the living body, so that changes in the difference of pressures on said two sides of said single flexible diaphragm means causes a motion of at least a portion of said single flexible diaphragm means;

(d) contact means connected to said housing for contacting the single flexible diaphragm mean for a predetermined relationship between the pressures on said single flexible diaphragm means thereby defining a mechanical contact reference position of said single flexible diaphragm means with respect to said housing for a predetermined relationship between said pressures on said single flexible diaphragm means;

(e) means having a preselected, detectable, variable parameter that is detectable by detection apparatus located outside of the living body, said means having a preselected, detectable variable parameter being so constructed and cooperatively connected to said single flexible diaphragm means that the variable parameter changes as a known function of the displacement with respect to said mechanical contact reference position of said single flexible diaphragm means and said displacement is a known function of the difference in pressures on the opposite sides of said single flexible diaphragm means; whereby when said sensor is implanted beneath the skin, said single flexible diaphragm means can be driven to said mechanical contact reference position by a pressure external to the living body applied to the skin adjacent to said sensor and said preselected, detectable, variable parameter can be determined at said mechanical contact reference position after implantation corresponding to said predetermined pressure relationship, and whereby the value of said preselected, detectable, variable parameter is a measure of the pressure in said bodily medium.

43. The sensor of claim 42, wherein said means allowing said second side of said single flexible diaphragm means to contact a bodily medium comprises a through opening in said housing, said single flexible diaphragm means extending across said through opening and being secured with respect to said housing.

44. An in vivo differential pressure sensor adapted for in vivo calibration after implantation, said sensor comprising:

(a) a housing which defines a chamber therein at least a portion of the wall of said housing being flexible so that changes in the pressures inside said chamber and outside said housing will cause movement of said flexible portion of said housing walls, said housing being adapted so that when implanted beneath the skin in the living body, said flexible portion of said housing wall can be placed in mechanical pressure communication with an interior portion of skin and whereby pressures external to the body can be communicated mechanically across the skin to said flexible portion of said housing wall;

(b) inlet means to said chamber allowing the entrance into said chamber of a bodily fluid, the pressure of which is to be measured when the sensor is implanted in the body;

(c) stop means within said housing adapted to make contact with, and thereby stop the movement of, said flexible portion of said housing wall for a predetermined pressure relationship between pressures inside said chamber and outside said housing;

(d) means within said housing having a preselected, detectable, variable parameter that is detectable by apparatus outside the living body, said means having a preselected, detectable variable parameter being so constructed and cooperatively connected to said single flexible diaphragm means that the preselected, detectable variable parameter changes as a known function of the pressures inside said chamber and outside said housing; and whereby the sensor can be calibrated in vivo by driving said flexible portion of wall into contact with said stop means by pressing on the skin adjacent to said sensor at which point the value of said preselected, detectable variable parameter can be determined, and whereby the change in said preselected, detectable variable parameter is a measure of the pressure of said bodily fluid.

* * * * *